(12) United States Patent
Boylan et al.

(10) Patent No.: US 8,309,299 B2
(45) Date of Patent: Nov. 13, 2012

(54) COMBINATION THERAPY AND METHOD FOR ASSESSING RESISTANCE TO TREATMENT

(75) Inventors: John Frederick Boylan, Bedminster, NJ (US); Wei He, New York, NY (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/098,527

(22) Filed: May 2, 2011

(65) Prior Publication Data

US 2011/0287025 A1    Nov. 24, 2011

Related U.S. Application Data

(60) Provisional application No. 61/346,247, filed on May 19, 2010.

(51) Int. Cl.
    *C12Q 1/68*     (2006.01)
    *G01N 33/53*    (2006.01)
    *G01N 33/68*    (2006.01)

(52) U.S. Cl. ............. 435/4; 435/6.1; 435/6.17; 435/7.1

(58) Field of Classification Search .................. None
    See application file for complete search history.

(56) References Cited

U.S. PATENT DOCUMENTS

| | | | |
|---|---|---|---|
| 2005/0054633 A1 | 3/2005 | Flohr et al. | |
| 2008/0280772 A1* | 11/2008 | Wong et al. | 506/9 |
| 2008/0300798 A1* | 12/2008 | McDevitt et al. | 702/19 |
| 2009/0181944 A1 | 7/2009 | Boylan et al. | |

FOREIGN PATENT DOCUMENTS

| | | |
|---|---|---|
| WO | WO01/27611 | 4/2001 |
| WO | WO2005/023772 | 3/2005 |

OTHER PUBLICATIONS

Lacroix et al, 2004. Breast Cancer Research and Treatment. 83: 249-289.*
Kobaek-Larsen et al, 2000. Comp Med. 50(1): 16-26.*
Freshney (Culture of Animal Cells, A Manual of Basic Technique, Alan R. Liss, Inc., 1983, New York, p4.*
Dermer (Bio/Technology, 1994, 12:320.*
PCT International Search Report PCT/EP2011/057909—mailed Jun. 16, 2011.
Luistro et al., "Cancer Research" 69(19):7672-7680 ( 2009).

* cited by examiner

*Primary Examiner* — Elizabeth C Kemmerer
(74) *Attorney, Agent, or Firm* — George W. Johnston; Patricia S. Rocha-Tramaloni; Gene J. Yao

(57) ABSTRACT

The present invention relates to a method for determining a subject's resistance to treatment with 2,2-dimethyl-N-((S)-6-oxo-6,7-dihydro-5H-dibenzo[b,d]azepin-7-yl)-N'-(2,2,3,3, 3-pentafluoro-propyl)-malonamide by measuring the levels a biomarker or biomarkers present in a biological sample obtained from the subject, the biomarker being IL6 and/or IL8. The present invention also relates to a combination therapy for a patient suffering from a proliferative disorder comprising administering to the patient 2,2-Dimethyl-N-((S)-6-oxo-6,7-dihydro-5H-dibenzo[b,d]azepin-7-yl)-N'-(2, 2,3,3,3-pentafluoro-propyl)-malonamide and an anti-IL6 and/or an anti-IL8 agent.

11 Claims, 14 Drawing Sheets

FIGURE 2
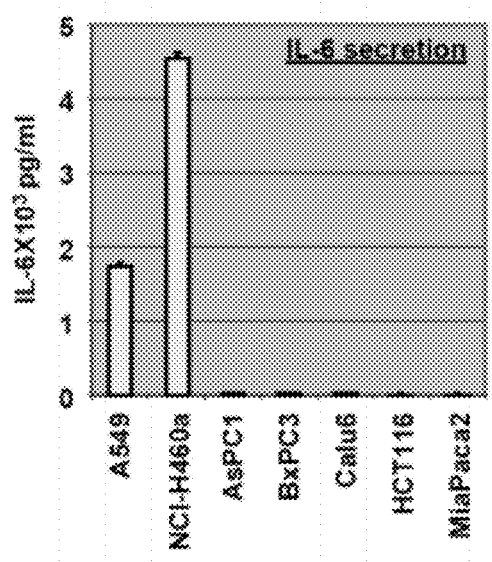
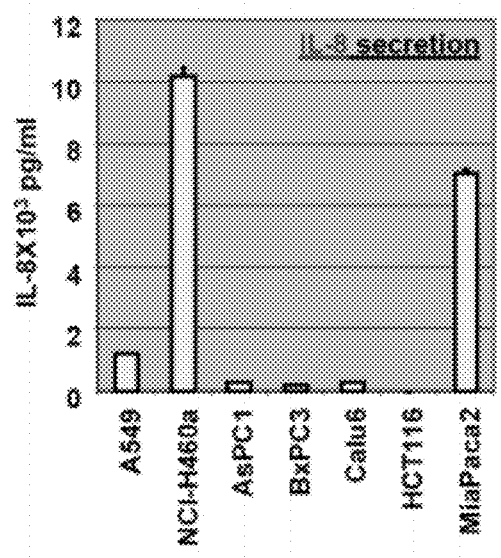

FIGURE 10
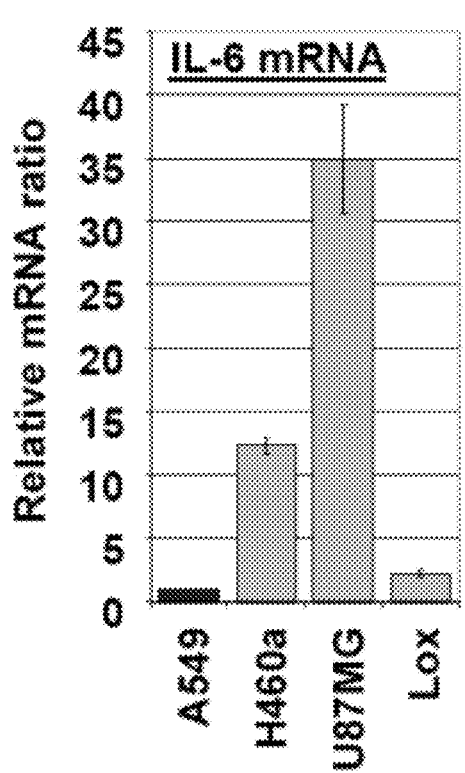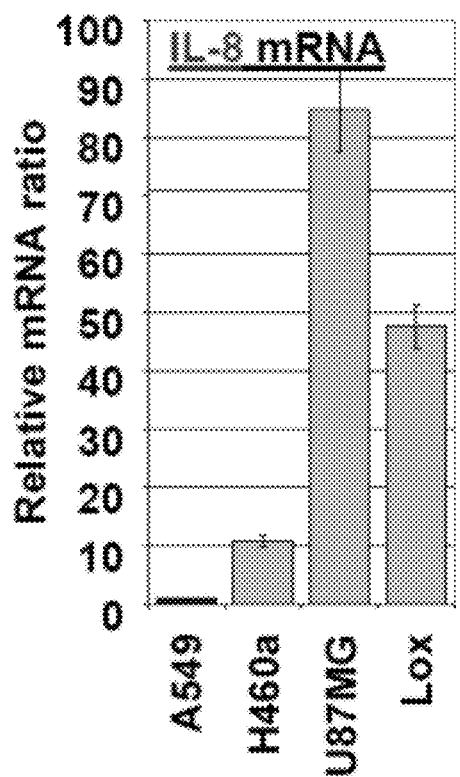

COMBINATION THERAPY AND METHOD FOR ASSESSING RESISTANCE TO TREATMENT

PRIORITY OF RELATED APPLICATION(S)

This application claims the benefit of U.S. Provisional Application No. 61/346,247, filed May 19, 2010, which is hereby incorporated by reference in its entirety.

FIELD OF THE INVENTION

The present invention relates to a method and a kit for determining a subject's resistance to treatment with 2,2-dimethyl-N-((S)-6-oxo-6,7-dihydro-5H-dibenzo[b,d]azepin-7-yl)-N'-(2,2,3,3,3-pentafluoro-propyl)-malonamide. The invention also relates to a combination therapy for treating a patient suffering from a proliferative disorder comprising administering 2,2-Dimethyl-N-((S)-6-oxo-6,7-dihydro-5H-dibenzo[b,d]azepin-7-yl)-N'-(2,2,3,3,3-pentafluoro-propyl)-malonamide and at least one of an anti-IL6 agent and an anti-IL-8 agent.

BACKGROUND OF THE INVENTION

The Notch protein is a transmembrane protein present in most organisms, including mammals, that has a role in regulating gene expression. Upon the binding of a ligand to the extracellular domain of Notch, the Notch protein is cleaved just outside the membrane by Tumor Necrosis Factor Alpha Converting Enzyme (TACE) releasing the extracellular domain which remains in interaction with the ligand. Then, gamma-secretase cleaves the protein just inside the membrane, releasing the intracellular domain (known as active intracellular Notch or "ICN"). The ICN translocates to the cell nucleus and activates transcription factor CSL, thus inducing gene transcription.

Faulty Notch signaling has been implicated in various disorders, including proliferative disorders. As such, inhibition of Notch signaling is an area of great interest in oncology. Gamma-secretase inhibition blocks the Notch signaling pathway and, as such, gamma-secretase inhibitors have anti-proliferative activity.

2,2-dimethyl-N-((S)-6-oxo-6,7-dihydro-5H-dibenzo[b,d]azepin-7-yl)-N'-(2,2,3,3,3-pentafluoro-propyl)-malonamide (also referred to herein as "Compound I") is a potent and selective inhibitor of gamma-secretase, inhibiting Notch signaling in tumor cells. It is known that xenografts treated with Compound I show reduced expression of genes associated with angiogenesis consistent with the ability of Compound I to inhibit tumor angiogenesis. Luistro et al., *Cancer Research*, 69:7672-80 (2009). Interestingly, these studies showed little change in the angiogenic gene profile for the H460a xenograft.

Interleukin-6 (IL6) and interleukin-8 (IL8) are powerful cytokines that play important roles in such diverse disorders such as infection and immunity, inflammation, autoimmune disease, and cancer. Applicants have found that elevated expression of each of IL6 and IL8 confers resistance to treatment with Compound I.

SUMMARY OF THE INVENTION

The present invention relates to a method for determining a subject's resistance to treatment with 2,2-Dimethyl-N-((S)-6-oxo-6,7-dihydro-5H-dibenzo[b,d]azepin-7-yl)-N'-(2,2,3,3-pentafluoro-propyl)-malonamide, comprising measuring the level of a biomarker present in a biological sample obtained from said subject, said biomarker being IL6 or IL8.

The present invention also relates to a kit for use in aiding in the determination of a subject's resistance to treatment with 2,2-Dimethyl-N-((S)-6-oxo-6,7-dihydro-5H-dibenzo[b,d]azepin-7-yl)-N'-(2,2,3,3,3-pentafluoro-propyl)-malonamide, wherein the kit comprises an agent for detecting a biomarker which is IL6 or IL8.

The present invention further relates to a method of treating a patient suffering from a proliferative disorder, comprising administering to the patient: (A) Compound I; and (B) an anti-IL6 or anti-IL8 agent.

A yet further aspect of the present invention is a kit comprising: (A) Compound I; and (B) an anti-IL6 or anti-IL8 agent.

BRIEF DESCRIPTION OF THE DRAWINGS

FIG. 2 depicts the amount of secreted IL6 and IL8 as measured from various cell lines using ELISA.

FIG. 10 depicts the levels of IL6 and IL8 encoding mRNA in various cell lines as measured using qRT-PCR.

DETAILED DESCRIPTION OF THE INVENTION

Definitions

Figure 1:
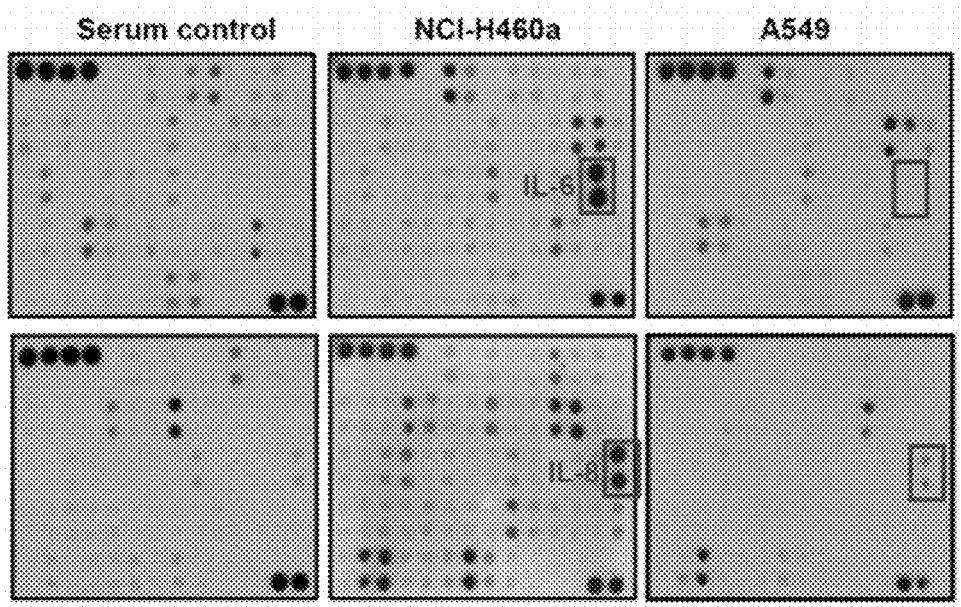
FIG. 1 depicts the results of a cytokine array assay performed on NCI-H460a and A549 cell lines.

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

As used herein, "Compound I" refers to 2,2-dimethyl-N-((S)-6-oxo-6,7-dihydro-5H-dibenzo[b,d]azepin-7-yl)-N'-(2,2,3,3,3-pentafluoro-propyl)-malonamide which is useful as a gamma-secretase inhibitor. Compound I has the following structure.

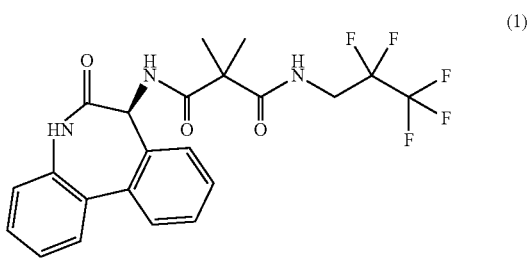

The term "biomarker" refers to an objectively measurable entity which serves as an indicator of a biological state.

The term "biological sample" refers to a portion (e.g., blood, serum, tissue, phlegm, urine, saliva) obtained from a subject, from which a biomarker may be measured.

The term "level" in reference to a biomarker refers to a measure of the concentration, activity, expression level, or amount of a biomarker present. The level may be determined quantitatively, for example by measuring the concentration or mass of the biomarker present in a sample, or for example by determining the quantity of mRNA encoding the biomarker that is expressed in a relevant cell population or tissue. Alternatively, the level may be determined more qualitatively, e.g., as being above or below a set threshold level. The threshold level may correspond to an average or median level of the biomarker in healthy subjects, or may correspond to the level at which a diagnosis of disease is made. A biomarker is said to be present at an "elevated level" if the level measured is above a set threshold level.

"Subject" includes mammals and birds. "Mammals" means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. The term "subject" does not denote a particular age or sex.

As used herein, the term "pharmaceutically acceptable carrier" indicates that the indicated carrier does not have properties that would cause a reasonably prudent medical practitioner to avoid administration thereof to a patient, taking into consideration the disease or conditions to be treated and the respective route of administration.

As used herein, the term "therapeutically effective" means an amount of a compound, or combination or composition, which is effective for producing a desired therapeutic effect upon administration to a patient, for example, to stem the growth, or result in the shrinkage, of a cancerous tumor or to increase the patient's life span.

The terms "cell proliferative disorder" and "proliferative disorder" refer to disorders that are associated with some degree of abnormal cell proliferation. In one embodiment, the proliferative disorder is cancer.

The terms "cancer" and "cancerous" refer to or describe the physiological condition in mammals that is typically characterized by unregulated cell growth/proliferation. Examples of cancer include, but are not limited to, colorectal cancer, melanoma, and thyroid cancer.

"Inhibiting cell growth or proliferation" means decreasing a cell's growth or proliferation by at least 10%, 20%, 30%, 40%, 50%, 60%, 70%, 80%, 90%, 95%, or 100%, and includes inducing cell death.

The phrase "substantially reduced" or "substantially different," as used herein, refers to a sufficiently high degree of difference between two numeric values (generally one associated with a molecule and the other associated with a reference/comparator molecule) such that one of skill in the art would consider the difference between the two values to be of statistical significance within the context of the biological characteristic measured by said values.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

Method for Determining Resistance

The present invention relates in part to a method for determining a subject's resistance to treatment with 2,2-dimethyl-N-((S)-6-oxo-6,7-dihydro-5H-dibenzo[b,d]azepin-7-yl)-N'-(2,2,3,3,3-pentafluoro-propyl)-malonamide (herein also referred to as "Compound I"), comprising measuring the level of a biomarker present in a biological sample obtained from said subject, said biomarker being IL6 or IL8.

In an embodiment of the invention, the level of biomarker present in said sample is compared with a threshold level for said biomarker and, if greater, said subject is considered to have in vivo resistance to treatment with Compound I. For purposes herein including in the claims, "in vivo resistance" refers to a reduced in vivo efficacious effect of treatment with Compound I.

In an embodiment of the invention, the biomarker is IL6 and said threshold level for IL6 is about 500 pg/ml.

In an embodiment of the invention, the biomarker is IL8 and said threshold level for IL8 is about 50 pg/ml.

The level of a biomarker can be determined based on the amount of the protein itself or by its respective mRNA.

Proteins can be measured directly by physical/chemical techniques such as gel electrophoresis, HPLC, mass spectroscopy, and proteomic techniques; immunoassay techniques, such as ELISA, competitive assays, sandwich assays, and the like; and by assays of biological activity (for example, as a ligand and/or an enzyme), by measuring that activity in the biological sample by methods known in the art, through two-hybrid assay systems, and the like. Commercial assays are available for many or most of the above-mentioned biomarkers, or are described in the art. Suitable biological samples include blood, serum, urine, and the like.

Alternatively, one can determine the level of mRNA that corresponds to the above-mentioned protein biomarkers. The determination of mRNA transcription level can be performed using any suitable quantitative or semi-quantitative method, including without limitation Northern blot; microarray techniques; RT-PCR, qRT-PCR and other quantitative and semi-quantitative DNA and mRNA amplification methods; and the like. For example, to perform RT-PCR, one can extract total RNA from the biological sample, treat it with DNase1 and convert it to cDNA using a reverse transcriptase such as Multiscribe reverse transcriptase (Applied Biosystems Inc., Foster City, Calif.). A cDNA "SYBR green" real-time quantitative PCR assay can then be performed using the cDNA as template, and analyzed using an ABI PRISM 7900 Sequence Detector.

In an embodiment of the present invention, the subject is a mammal, for example a human.

In an embodiment of the invention, the biomarker measured is IL6.

In an embodiment of the invention, the biomarker measured is IL8.

In an embodiment of the invention, both IL6 and IL8 are measured.

In an embodiment of the invention, the biological sample is blood

In an embodiment of the invention, the biological sample is serum.

In an embodiment of the invention, the biological sample is urine.

In an embodiment of the invention, the biomarker is measured by measuring the amount of protein present in said sample.

In an embodiment of the invention, the biomarker is measured by measuring the level of mRNA encoding the biomarker.

Kit for Determining Resistance

The present invention also relates to a kit for use in aiding in the determination of a subject's resistance to treatment with 2,2-Dimethyl-N-((S)-6-oxo-6,7-dihydro-5H-dibenzo[b,d]azepin-7-yl)-N'-(2,2,3,3,3-pentafluoro-propyl)-malonamide, wherein the kit comprises an agent for detecting a biomarker which is IL6 or IL8 in a biological sample obtained from the subject.

Combination Therapy

The present invention relates to a method of treating a patient suffering from a proliferative disorder, comprising administering to the patient: (A) Compound I; and (B) an anti-IL6 or anti-IL8 agent. In an embodiment of the present invention, both an anti-IL6 and an anti-IL8 agent are administered.

Treatment of a proliferative disorder shall be understood to include maintaining or decreasing tumor size, inducing tumor regression (either partial or complete), inhibiting tumor growth, and/or increasing the life span of a patient suffering from said disorder.

The present invention also relates to a kit comprising: (A) Compound I; and (B) an anti-IL6 or anti-IL8 agent. In an embodiment of the present invention, the kit comprises both an anti-IL6 agent and an anti-IL8 agent.

In an embodiment of the invention, the proliferative disorder is a solid tumor.

In another embodiment of the invention, the solid tumor is selected from the group consisting of: brain, liver, prostate, ovarian, pancreatic, skin, breast, colorectal, lung, and prostate tumors.

In another embodiment of the invention, the solid tumor is selected from the group consisting of: breast, colorectal, lung, and prostate tumors.

In an embodiment of the present invention, the anti-IL6 agent is administered in an amount that is effective in reducing the level of IL6 in the patient.

In an embodiment of the present invention, the anti-IL8 agent is administered in an amount that is effective in reducing the level of IL8 in the patient.

In an embodiment of the present invention, the anti-IL6 agent is an anti-IL6 antibody.

In an embodiment of the present invention, the anti-IL8 agent is an anti-IL8 antibody.

In an embodiment of the present invention, the anti-IL6 agent is a nucleic acid which interferes with the expression of a nucleic acid encoding IL6. The nucleic acid which interferes with the expression of a nucleic acid encoding IL6 may, for example, be an antisense RNA. The nucleic acid may also be, for example, a shRNA or a siRNA.

In an embodiment of the present invention, the anti-IL8 agent is a nucleic acid which interferes with the expression of a nucleic acid encoding IL8. The nucleic acid which interferes with the expression of a nucleic acid encoding IL8 may, for example, be an antisense RNA. The nucleic acid may also be, for example, a shRNA or a siRNA.

In an embodiment of the method of the present invention, Compound I is administered in an amount that is therapeutically effective for the treatment of a proliferative disorder. That amount may, for example, be from about 400 ng-hr/ml to about 9000 ng-hr/ml, from about 1100 ng-hr/ml to about 4100 ng-hr/ml, or from about 1380 ng-hr/ml to about 2330 ng-hr/ml. In embodiments of the present invention, Compound I may be administered in an amount of from about 400 ng-hr/ml to about 9000 ng-hr/ml administered over a period of up to about 21 days, from about 1100 ng-hr/ml to about 4100 ng-hr/ml administered over a period of up to about 21 days, from about 1380 ng-hr/ml to about 2330 ng-hr/ml administered over a period of up to about 21 days.

In an embodiment of the method of the present invention, Compound I is administered once daily on days 1, 2, 3, 8, 9, and 10 of a 21 day cycle. In another embodiment, administration may be once daily on days 1 to 7 of a 21 day cycle. In a further embodiment, administration may be once daily on a daily basis.

In embodiments of the method and kit of the present invention, Compound I is in a pharmaceutical oral unit dosage form.

In an embodiment of the method of the present invention, the patient is also subjected to radiotherapy.

In an embodiment of the method of the present invention, Compound I is administered once daily on days 1, 2, 3, 8, 9, and 10 of a 21 day cycle in an amount of from about 400 ng-hr/ml to about 9000 ng-hr/ml.

In an embodiment of the method of the present invention, Compound I is administered once daily on days 1-7 of a 21 day cycle in an amount of from about 400 ng-hr/ml to about 9000 ng-hr/ml.

In an embodiment of the present invention, the anti-IL6 antibody is administered in an amount that is effective in reducing the level of IL6 in the patient.

In an embodiment of the method of the present invention, anti-IL6 antibody is administered in an amount of about 1 to about 100 mg/kg twice weekly.

In an embodiment of the method of the present invention, anti-IL6 antibody is administered in an amount of about 1 to about 50 mg/kg twice weekly.

In an embodiment of the method of the present invention, anti-IL6 antibody is administered in an amount of about 10 to about 30 mg/kg twice weekly.

In an embodiment of the method of the present invention, anti-IL6 antibody is administered in an amount of about 20 mg/kg twice weekly.

In an embodiment of the present invention, the anti-IL8 antibody is administered in an amount that is effective in reducing the level of IL8 in the patient.

In an embodiment of the method of the present invention, anti-IL8 antibody is administered in an amount of about 1 to about 100 mg/kg twice weekly.

In an embodiment of the method of the present invention, anti-IL8 antibody is administered in an amount of about 1 to about 50 mg/kg twice weekly.

In an embodiment of the method of the present invention, anti-IL8 antibody is administered in an amount of about 10 to about 30 mg/kg twice weekly.

In an embodiment of the method of the present invention, anti-IL8 antibody is administered in an amount of about 20 mg/kg twice weekly.

In an embodiment of the present invention, the anti-IL6 shRNA is administered in an amount that is effective in reducing the level of IL6 in the patient.

In an embodiment of the present invention, the anti-IL8 shRNA is administered in an amount that is effective in reducing the level of IL8 in the patient.

In an embodiment of the present invention, the anti-IL6 siRNA is administered in an amount that is effective in reducing the level of IL6 in the patient.

In an embodiment of the present invention, the anti-IL8 siRNA is administered in an amount that is effective in reducing the level of IL8 in the patient.

The dosage levels of Compound I, the anti-IL6 agent, and/or the anti-IL8 agent may be modified by the physician to be lower or higher than that stated herein depending on the needs of the patient, and the reaction of the patient to the treatment.

EXAMPLES

The following preparations and examples are given to enable those skilled in the art to more clearly understand and practice the present invention. They should not be considered as limiting the scope of the invention, but merely as being illustrative and representative thereof.

Example 1

This example shows the response of various different xenograft models to treatment with Compound I.

Female nu/nu (nude) mice obtained from Charles River Laboratories (Wilmington, Mass.) or female SCID-beige mice (Taconic, Germantown, N.Y.) were used (10 mice/group) when they were approximately 8 to 14 weeks old and weighed approximately 23 to 25 grams. All animal experiments were performed in accordance with protocols approved by the Roche Animal Care and Use Committee (RACUC).

The human cancer cell lines LOVO, BxPC3, HCT-116, A549, AsPC-1, MiaPaCa-2, and Calu-6 were purchased from the American Type Culture Collection. The H460a cell line was a gift from Dr. Jack Roth (M. D. Anderson Medical Center).

For xenograft implantation, cells were harvested using 0.05% trypsin, washed and centrifuged in culture medium, and resuspended in either a 1:1 mixture of phosphate buffered saline (PBS) and Matrigel (BxPC-3) or PBS alone (A549, H460a, LOVO, Calu-6, HCT-116, MiaPaca-2, and AsPC-1) at a concentration of $1.5$-$5 \times 10^7$ cells per mL. A volume of 0.2 mL cell suspension ($7.5 \times 10^6$ cells for A549, $1 \times 10^7$ cells for H460a, $3 \times 10^6$ cells for Calu-6 and HCT116, $5 \times 10^6$ cells for BxPC3 and AsPC-1, $6 \times 10^6$ cells for MiaPaca-2, and $5 \times 10^6$ for LOVO) per mouse was implanted subcutaneously in the right flank. All xenograft models were implanted into nude mice with the exception of BxPC3, which was implanted into SCID-beige mice. Tumors were allowed to grow for 8 to 26 days post implant when mean volume reached ~100-150 mm$^3$, after which animals were randomized into treatment groups.

Compound I (synthesized according to the procedure described in WO2005/023772) was formulated as a suspension in 1.0% Klucel in water with 0.2% Tween®-80 for oral (po) administration. Formulated compound and vehicle were prepared weekly and stored at 4° C. In the Calu-6 xenograft model, Compound I was dosed at 60 mg/kg daily every other week for 4 weeks (7+/7−×2 cycles). All other xenograft models were dosed with Compound I at 10 mg/kg daily.

Tumor measurements and mouse weights were taken twice per week. Statistical analysis was determined by Mann-Whitney Rank Sum Test, 1-way ANOVA, and post hoc Bonferroni t-test (SigmaStat, version 2.0, Jandel Scientific, San Francisco, Calif.). Differences between groups were considered significant when the probability value (p) was $\leq 0.05$.

Tumor growth inhibition (TGI %) was measured 21 days following the commencement of the treatment. The results were as shown below in Table 1.

TABLE 1 in vivo activity in xenograft models

| Tumor Type | TGI % |
|---|---|
| LOVO (colon) | 83 |
| BxPC3 (pancreatic) | 82 |
| HCT-116 (colon) | 76 |
| A549 (NSCLC) | 70 |
| AsPC-1 (pancreatic) | 58 |
| MiaPaCa-2 (pancreatic) | 53 |
| Calu-6 (NSCLC) | 42 |
| H460a (NSCLC) | 8 |

As can be seen, the H460a xenograft exhibited by far the least amount of tumor growth inhibition following treatment with Compound I (8%).

Example 2

After identifying, in Example 1, that the H460a xenograft model exhibited by far the least amount of tumor growth inhibition following treatment with Compound I, a cytokine array assay was conducted on both the H460a and A549 NSCLC cell lines to determine if there were any biomarkers that set the H460a cell line apart.

Cytokine arrays were purchased from RayBiotech, Inc. (Norcross, Ga.) and used according to the manufacture's protocol. Cells were grown for 5 days, cell media was harvested and detached cells were removed by centrifugation. Four milliliters of media was incubated overnight with the array followed by multiple PBS/Tween washes followed by development of the signal.

It was determined that the H460a cell line expressed higher levels of both IL6 and IL8 than A549 or a serum control. See FIG. 1.

Example 3

Expression of IL6 and IL8 was then quantified in the BxPC3, HCT-116, A549, AsPC-1, MiaPaCa-2, and Calu-6 cell lines by measuring the level of secreted IL6 and IL8 protein using ELISA.

The IL6 ELISA kits are purchased from Bender MedSystems (BMS213/2 or BMS213INST). The IL8 ELISA kits are purchased from Bender MedSystems (BMS204/3INST) or R&D Systems (D8000C). To measure secreted IL6 and IL8 in tissue culture medium, cells were seeded at a density of half a million in 35 mm plate. The next day, the cells were washed with 2 ml PBS, then replenished with 1 ml fresh medium. After 24 hours, the medium was harvested and immediately used for ELISA analysis.

As seen from the results (see FIG. 2), H460a cells secrete higher amounts of IL6 and IL8 protein than the other cell lines tested including 4-fold higher IL6 protein and 10-fold higher IL8 protein as compared with A549 cells.

Example 4

Expression of IL6 and IL8 was then quantified in the BxPC3, HCT-116, A549, AsPC-1, MiaPaCa-2, and Calu-6 cell lines by measuring the level of mRNA using qRT-PCR. RNA isolation, and reverse transcription-PCR (RT-PCR) were done using standard laboratory techniques. The catalogue numbers for each probe set were Hes1 (Hs00172878_m1), ACTB (4333762F), IL6 (Hs00174131_m1), IL8 (Hs00174103_m1) and 18S (4319413E).

Figure 3:
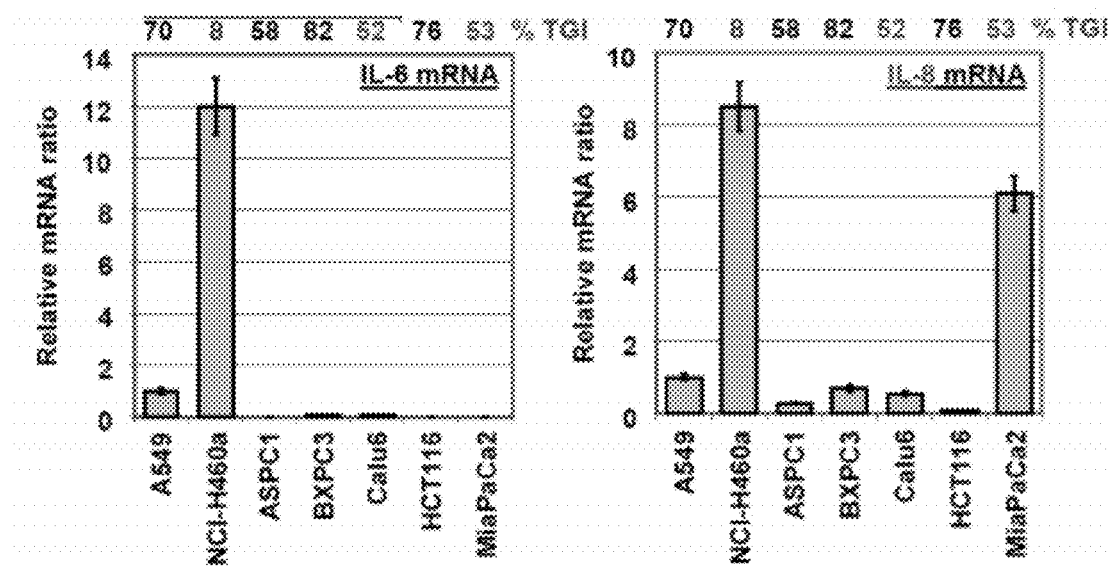
FIG. 3 depicts the amount of mRNA encoding IL6 and IL8 as measured from various cell lines using qRT-PCR.

As seen from the results (see FIG. 3), H460a cells express higher amounts of IL6 and IL8 mRNA than the other cell lines tested including 12-fold higher IL6 mRNA and 8-fold higher IL8 mRNA as compared with A549 cells.

Example 5

In order to test if expression of IL6 or IL8 modulates the efficacy of Compound I treatment, A549 cells lines which overexpress IL6 or IL8 were engineered and used to make xenograft models which were studied to determine if such overexpression alters the sensitivity of the cells to Compound I treatment.

IL6 and IL8 lentiviruses were made using IL6 and IL8 plasmids (available from Genecopoeia, Rockville, Md., USA), respectively. A549 cells were divided into three groups with one group receiving a vector control, one group being infected with the IL6 lentivirus and the third group being infected with the IL8 lentivirus. The later two groups formed cell pools with stable expression of exogenous IL6 and IL8, respectively.

Figure 4:
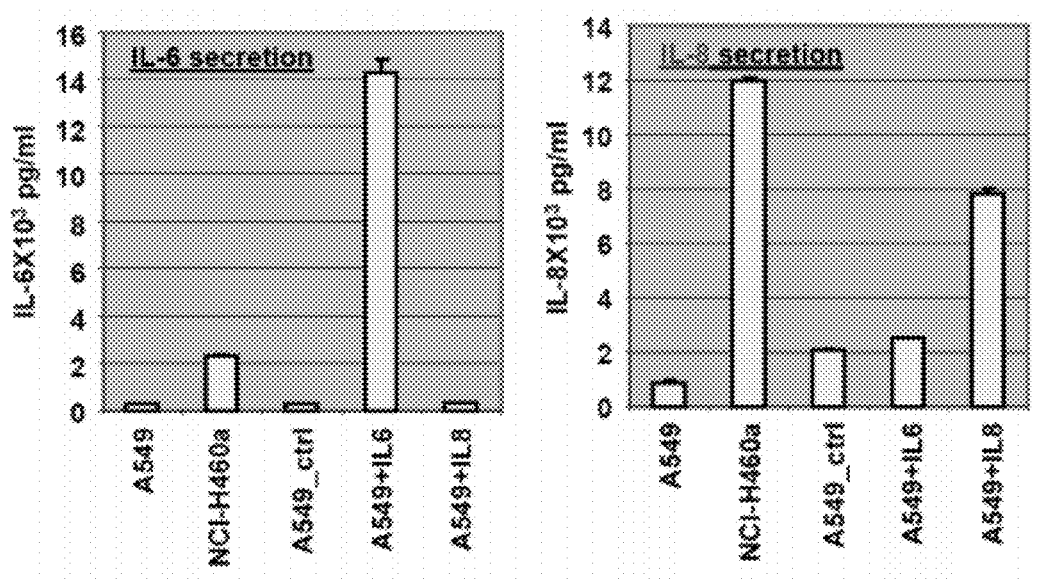
FIG. 4 depicts the amount of secreted IL6 and IL8 as measured from H460a cells, A549 parental cells, A549 control cells, A549 IL6 overexpressing cells and A549 IL8 overexpressing cells using ELISA.

The overexpression of IL6 and IL8 protein was quantified by ELISA. See FIG. 4. A549 cells overexpressing IL6 secreted 7-fold higher IL6 compared to H460a. A549 cells overexpressing IL8 secreted slightly less IL8 protein than H460a. A549 cells overexpressing IL6 or IL8 have a similar morphology as A549 vector control cells.

A portion of the IL6 overexpressing A549 cells and the IL8 overexpressing A549 cells were then combined to form a fourth group containing a 1:1 mixture of such cells.

A549 cells receiving the vector control, A549 cells overexpressing IL6, A549 cells overexpressing IL8, and a 1:1 mixture of A549 cells overexpressing IL6 and A549 cells overexpressing IL8 were seeded on a six well plate with each group being seeded in a well at about $1 \times 10^5$ per well on day 0. At days 4, 6, 10 and 12, all cells were trypsinized and counted, then replated for further propagation at the same dilution. The control cells were set arbitrarily as 100% growth. Growth of all the other cell types was expressed as a ratio to growth of control cells. All cell lines tested displayed a similar growth rate. See Table 2.

TABLE 2

|  | Day 0 | Day 4 | Day 6 | Day 10 | Day 12 |
| --- | --- | --- | --- | --- | --- |
| A549_ctrl | 100 ± 25 | 100 ± 2 | 100 ± 1 | 100 ± 2 | 100 ± 17 |
| A549 + IL6 | 90 ± 5 | 109 ± 6 | 112 ± 20 | 98 ± 5 | 97 ± 6 |

TABLE 2-continued

|  | Day 0 | Day 4 | Day 6 | Day 10 | Day 12 |
| --- | --- | --- | --- | --- | --- |
| A549 + IL8 | 84 ± 12 | 91 ± 12 | 118 ± 6 | 77 ± 6 | 78 ± 4 |
| A549 + IL6 & 8 | 64 ± 14 | 74 ± 14 | 72 ± 17 | 71 ± 1 | 77 ± 5 |

The in vivo effect of IL6 and IL8 overexpression on Compound I efficacy was evaluated for each of these cell groups.

Cells from the aforementioned four groups and parental A549 and H460a cells were used to make xenograft models using the procedure described in Example 1.

The mice were randomized into different treatment groups (10 mice/group): parental A549 mice receiving vehicle (Klucel and Tween) once daily, parental A549 mice receiving Compound I at 10 mg/kg once daily, parental A549 mice receiving Taxol® at 30 mg/kg four times daily, vector control A549 mice receiving vehicle (Klucel and Tween) once daily, vector control A549 mice receiving Compound I at 10 mg/kg once daily, vector control A549 mice receiving Taxol® at 30 mg/kg four times daily, IL6-overexpressing A549 mice receiving vehicle (Klucel and Tween) once daily, IL6-overexpressing A549 mice receiving Compound I at 10 mg/kg once daily, IL6-overexpressing A549 mice receiving Taxol® at 30 mg/kg four times daily, IL8-overexpressing A549 mice receiving vehicle (Klucel and Tween) once daily, IL8-overexpressing A549 mice receiving Compound I at 10 mg/kg once daily, IL8-overexpressing A549 mice receiving Taxol® at 30 mg/kg four times daily, A549 mice containing a 1:1 xenograft mixture of IL-6 and IL-8 overexpressing A549 cells receiving vehicle (Klucel and Tween) once daily, A549 mice containing a 1:1 xenograft mixture of IL-6 and IL-8 overexpressing A549 cells receiving Compound I at 10 mg/kg once daily, and A549 mice containing a 1:1 xenograft mixture of IL-6 and IL-8 overexpressing A549 cells receiving Taxol® at 30 mg/kg four times daily, H460a mice receiving vehicle (Klucel and Tween) once daily, H460a mice receiving Compound I at 10 mg/kg once daily, and H460a mice receiving Taxol® at 30 mg/kg four times daily.

Figure 5:
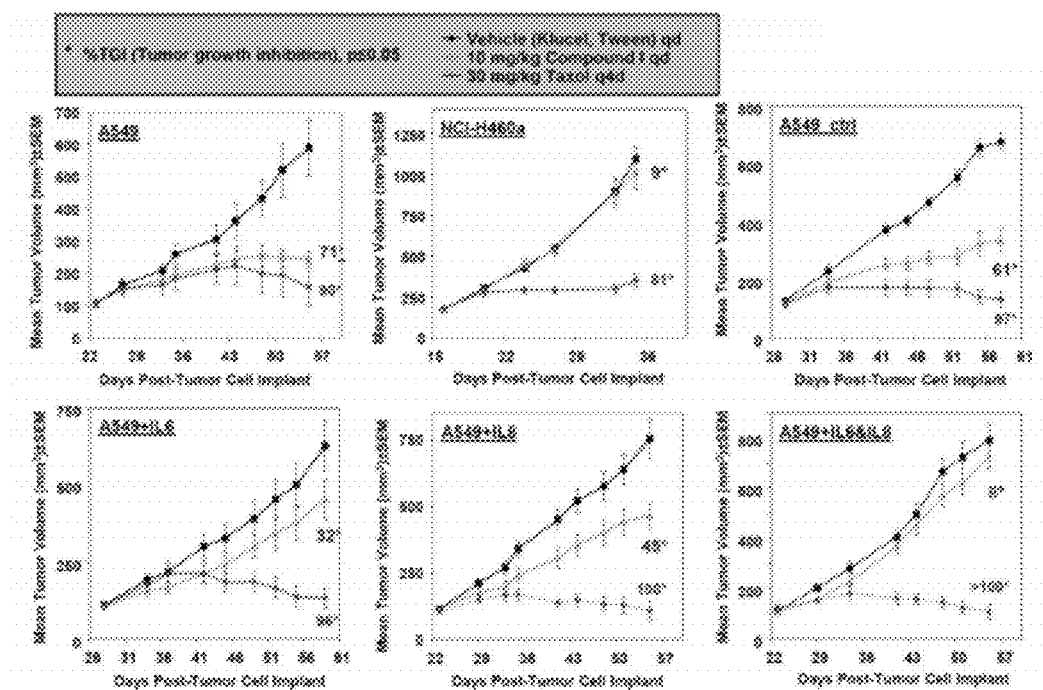
FIG. 5 depicts the effect of treatment with Compound I and the effect of treatment with Taxol® on tumor growth in xenograft models receiving: H460a cells, A549 parental cells, A549 control cells, A549 IL6 overexpressing cells, A549 IL8 overexpressing cells, and a 1:1 mixture of A549 IL6 overexpressing cells and A549 IL8 overexpressing cells.

Xenograft tumors from H460a (high levels of both IL6 and IL8) treated with 10 mg/kg Compound I once daily produced a 9% TGI after 21 days. This resistance was in clear contrast to the 71% TGI observed for A549 tumors and 61% TGI for A549 vector control tumors (low level of IL6 and IL8) consistent with previous experiments. Overexpression of IL6 or IL8 in A549 reduced the TGI to 32% and 45%, respectively. Tumors initiated with a 1:1 mixture of A549 overexpressing IL6 or IL8 demonstrated full resistance to Compound I (8% TGI), in line with the resistance of the parental H460a xenograft. Taxol® was included as a positive drug control showing consistent TGI across the various models. See FIG. 5.

The resistance of A549 overexpressing IL6 or IL8 to Compound I was not caused by a loss of Notch inhibition since downregulation of Hes1 mRNA following in vitro Compound I treatment, the hallmark of Notch signaling blockage, was properly maintained in these cells.

Example 6

This example describes a study conducted to explore whether IL8 expression is required for maintaining the resistance of H460a cells.

Figure 6:
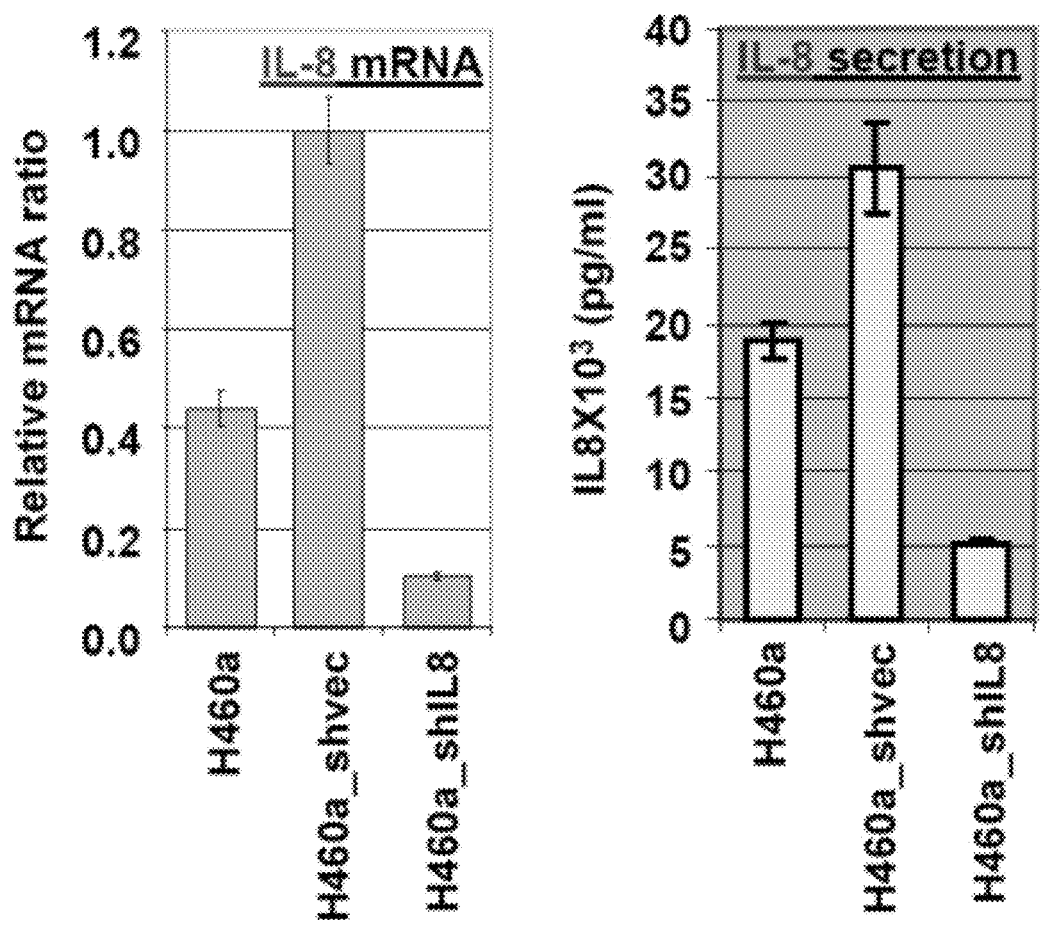
FIG. 6 depicts the amount of mRNA encoding IL8 and the amount of secreted IL8 as measured from parental H460a cells, H460a cells receiving a control vector, and IL8-knockdown H460a cells.

Lentiviruses were made using pLKO.1-based anti-IL8 shRNA (purchased from Open Biosystems) and used to stably knockdown IL8 expression in H460a cells. As shown in FIG. 6, shRNA gave a 75% knockdown of IL8 expression (both mRNA and protein) compared to H460a parental cells. IL8-knockdown H460a cells, however, still had more than 2-fold higher IL8 levels compared to A549 cells.

Parental H460a cells and IL8-knockdown H460a cells were then implanted as xenografts in mice using the procedures described in Example 1. The mice were then randomized into different treatment groups (10 mice/group): H460a xenograft mice receiving vehicle once daily, H460a xenograft mice receiving Compound I at 10 mg/kg once daily, IL8-knockdown H460a xenograft mice receiving vehicle once daily, and IL8-knockdown H460a xenograft mice receiving Compound I at 10 mg/kg once daily.

Figure 7:
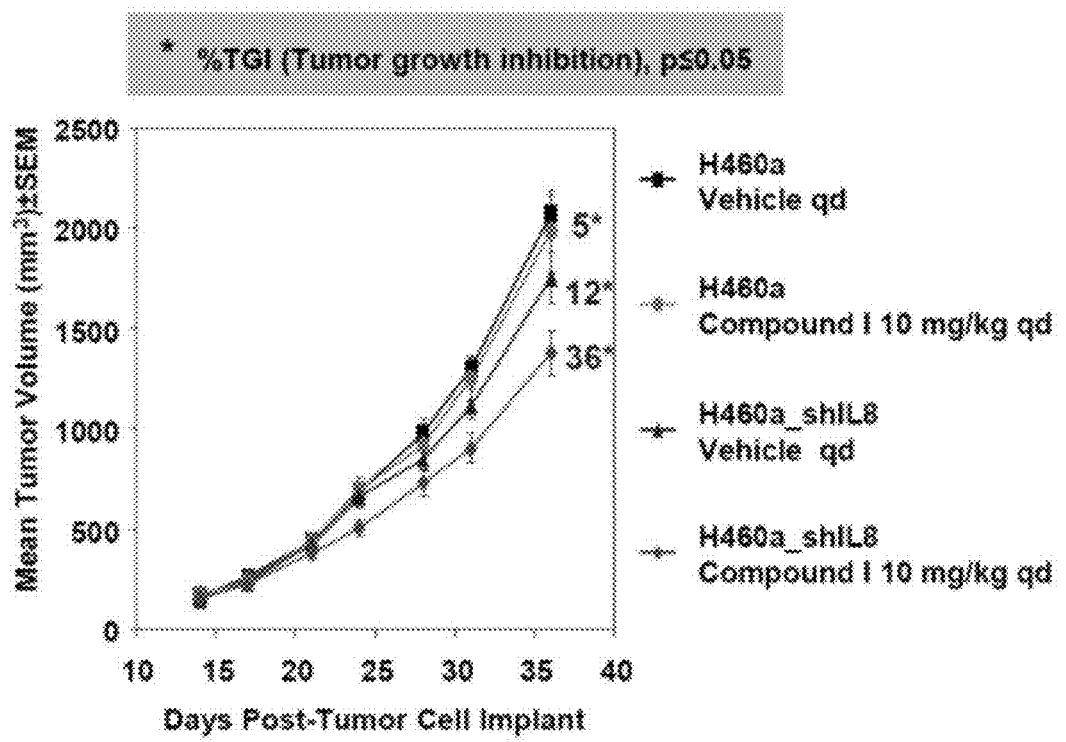
FIG. 7 depicts the effect on tumor growth of Compound I treatment as measured in H460a and IL-8 knockdown H460a xenograft models.

As shown in FIG. 7, when treated with Compound I at 10 mg/kg once daily for 21 days, tumors derived from IL8-knockdown H460a cells showed improved responsiveness as compared with tumors from parental H460a cells (5% TGI vs 24% TGI).

Example 7

This example describes a further study conducted to explore whether IL8 expression is required for maintaining the resistance of H460a cells.

Neutralizing anti-IL8 antibody was purchased from R&D systems (Catalog number: MAB208). This antibody was first tested in vitro and no growth inhibition was observed from H460a cells treated with this antibody.

H460a xenograft models were made using the procedure described in Example 1. The mice were then randomized into different treatment groups (10 mice/group): H460a xenograft mice receiving vehicle twice weekly, H460a xenograft mice receiving Compound I at 10 mg/kg once daily, H460a xenograft mice receiving anti-IL8 antibody at 20 mg/kg twice weekly, and H460a xenograft mice receiving Compound I at 10 mg/kg once daily and anti-IL8 antibody at 20 mg/kg twice weekly.

Figure 8:
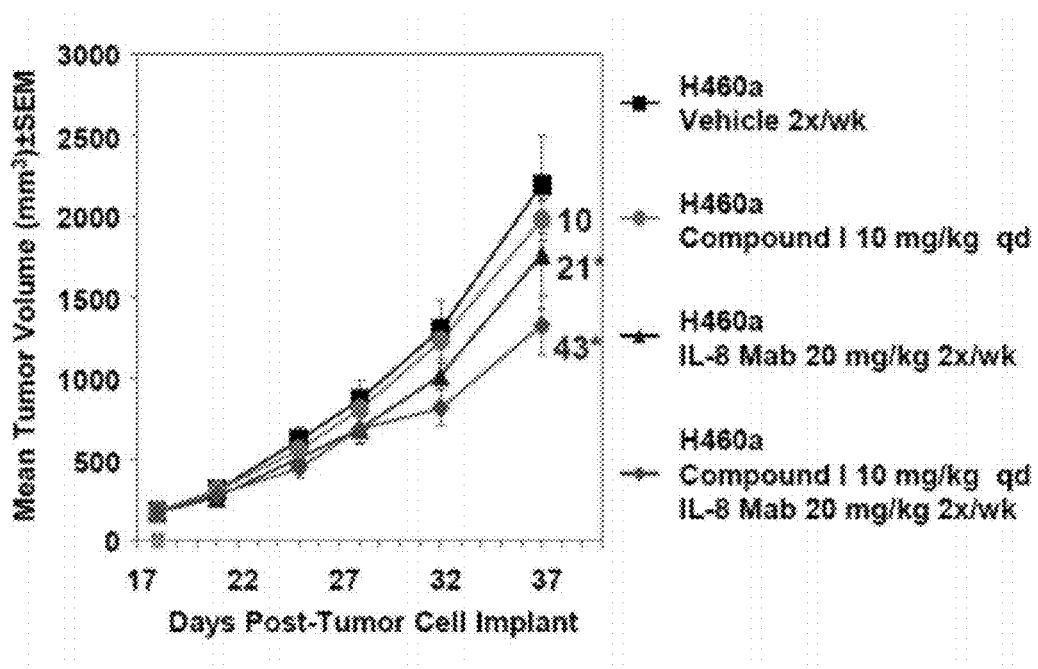
FIG. 8 depicts the effect on tumor growth in H460a xenograft models of treatment with Compound I, treatment with anti-IL8 antibody, and combination therapy with Compound I and IL-8 antibody.

The combination of the antibody with Compound I improved the sensitivity of H460a tumors to Compound I (10% TGI vs 43% TGI). This is consistent with the previous data utilizing IL8 shRNA. See FIG. 8.

Example 8

This example describes a study conducted to explore whether IL6 expression is required for maintaining the resistance of H460a cells.

Neutralizing anti-IL6 antibody was purchased from R&D systems (Catalog number: MAB2061). This antibody was first tested in vitro and no growth inhibition was observed from H460a cells treated with this antibody.

H460a xenograft models were made using the procedure described in Example 1. The mice were then randomized into different treatment groups (10 mice/group): H460a xenograft mice receiving vehicle twice weekly, H460a xenograft mice receiving Compound I at 10 mg/kg once daily, H460a xenograft mice receiving anti-IL6 antibody at 20 mg/kg twice weekly, and H460a xenograft mice receiving Compound I at 10 mg/kg once daily and anti-IL6 antibody at 20 mg/kg twice weekly.

Figure 9:
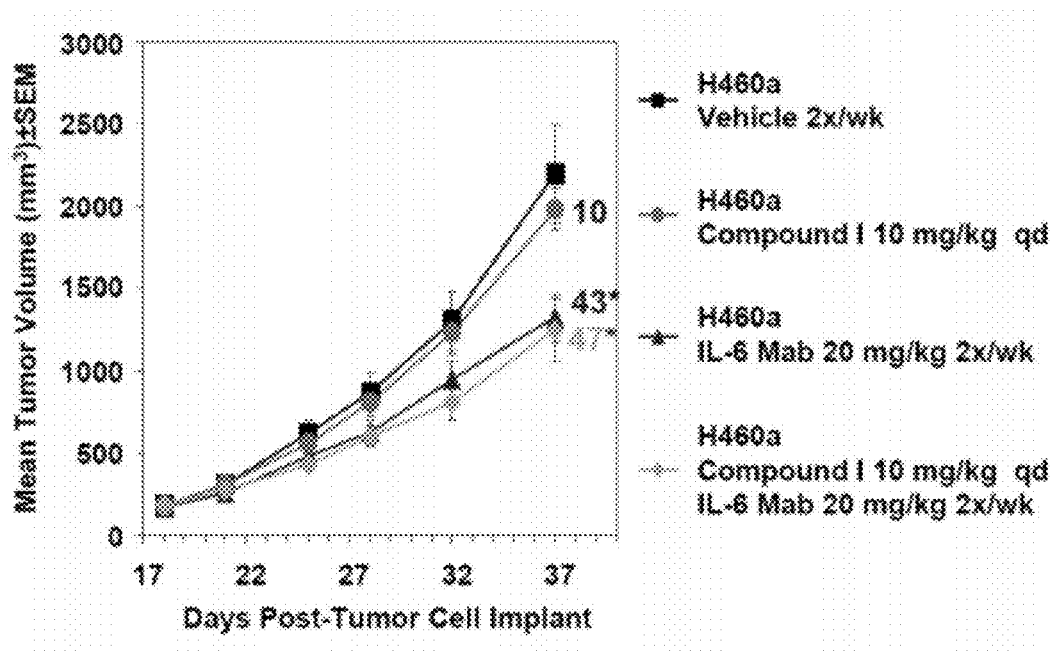
FIG. 9 depicts the effect on tumor growth in H460a xenograft models of treatment with Compound I, treatment with anti-IL6 antibody, and combination therapy with Compound I and IL-6 antibody.

The combination of the antibody with Compound I improved the sensitivity of H460a tumors to Compound I (43% TGI vs 47% TGI). See FIG. 9.

Example 9

An important aspect of any response marker is the ability to successfully prospectively identify responder and non-responder tumor types. In this example, different cell lines were analyzed to determine if they had a high expression level of IL6 and/or IL8. Then, xenografts were made using cells expressing high levels of IL6 and IL8 (and thus predicted to be non-responders to Compound I treatment). The xenograft models were then treated with Compound I to see if the high levels of IL6 and IL8 had any effect on the efficacy of the treatment.

Figure 11:
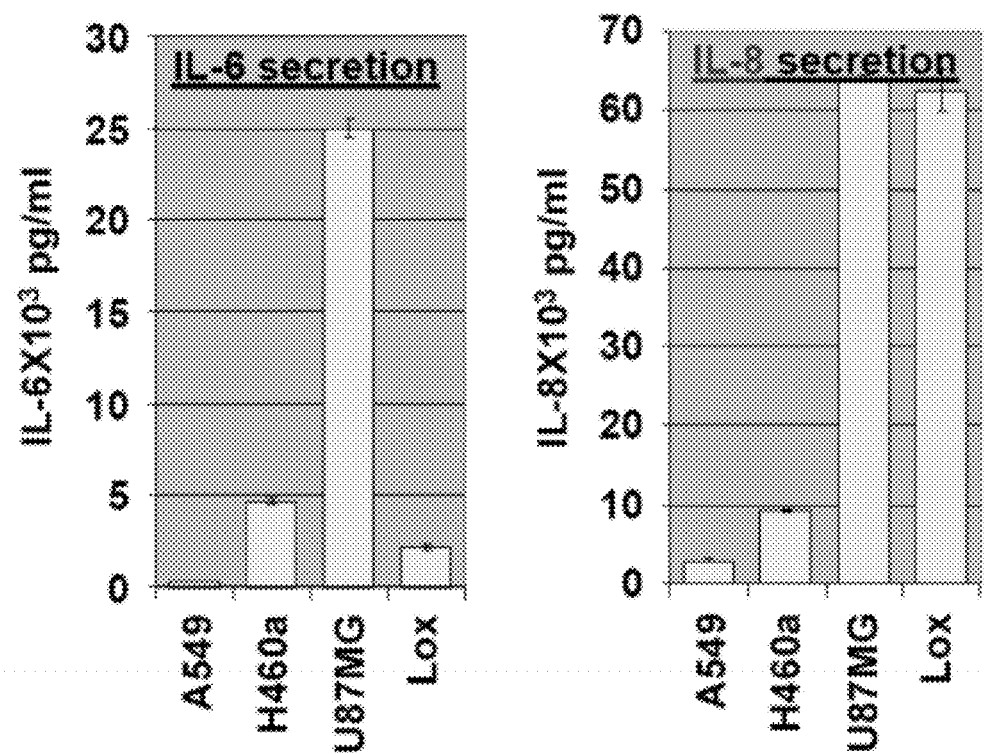
FIG. 11 depicts the levels of IL6 and IL8 secreted by various cell lines as measured using ELISA.

Approximately one hundred cell lines across multiple tumor types were screened for expression of IL6 and IL8 by qRT-PCR. About 13% of the cell lines had at least 10-fold higher expression of IL6 or IL8 than A549. Two cell lines, U87MG (glioblastoma), which expresses high levels of IL6 (35 fold higher IL6 mRNA than A549) and IL8 (85 fold higher IL8 mRNA than A549), and LOX (melanoma), which expresses a higher levels of IL8 (50-fold higher IL8 mRNA than A549) and IL6 (2-fold higher IL6 mRNA than A549) relative to A549 (FIG. 10), were selected for further study. The higher expression level of IL6 and/or IL8 from these two cell lines were further confirmed by ELISA (FIG. 11).

The human cancer cell lines U87MG and LOX were purchased from the American Type Culture Collection.

Xenograft models were then made using the U87MG and LOX cell lines.

Xenografts were implanted in female nu/nu (nude) mice obtained from Charles River Laboratories (Wilmington, Mass.) (10 mice/group) when they were approximately 8 to 14 weeks old and weighed approximately 23 to 25 grams. All animal experiments were performed in accordance with protocols approved by the Roche Animal Care and Use Committee (RACUC).

For xenograft implantation, cells were harvested using 0.05% trypsin, washed and centrifuged in culture medium, and resuspended in either a 1:1 mixture of phosphate buffered saline (PBS) and Matrigel (U87MG) or PBS alone (LOX) at a concentration of $1.5$-$5 \times 10^7$ cells per mL. A volume of 0.2 mL cell suspension ($5 \times 10^6$ cells for U87MG, $2 \times 10^6$ cells for LOX) per mouse was implanted subcutaneously in the right flank. Tumors were allowed to grow for 8 to 26 days post implant when mean volume reached ~100-150 mm$^3$, after which animals were randomized into treatment groups: U87MG xenograft mice receiving vehicle (Klucel and Tween) once daily, U87MG xenograft mice receiving Compound I at 10 mg/kg once daily for 21 days, LOX xenograft mice receiving vehicle (Klucel and Tween) once daily, and LOX xenograft mice receiving Compound I at 10 mg/kg once daily for 11 days.

Figure 12:
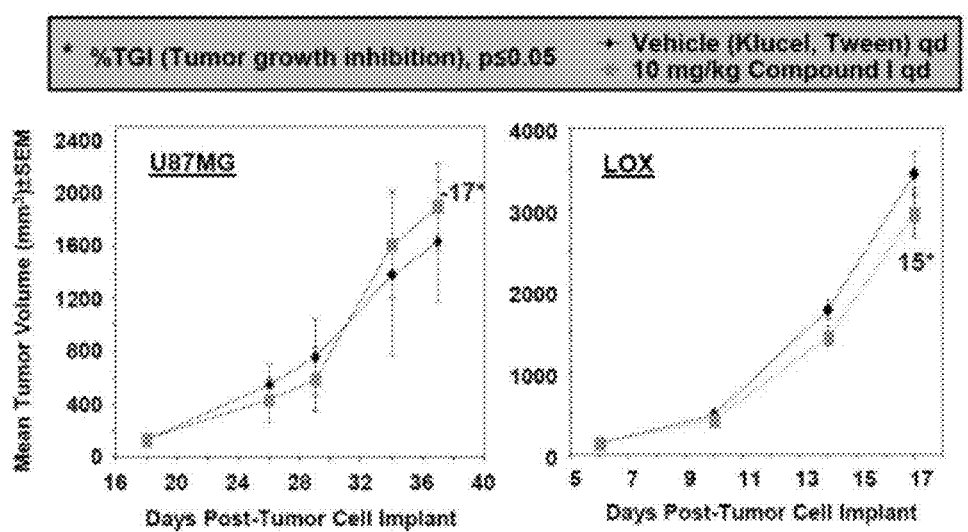
FIG. 12 depicts the downregulation of HesI mRNA in U87MG and LOX cells following treatment with Compound I.

Both U87MG and LOX models proved resistant to treatment with Compound I as predicted, with a −17% TGI for U87 MG tumors and a 15% TGI for LOX tumors. See FIG. 12.

Figure 13:
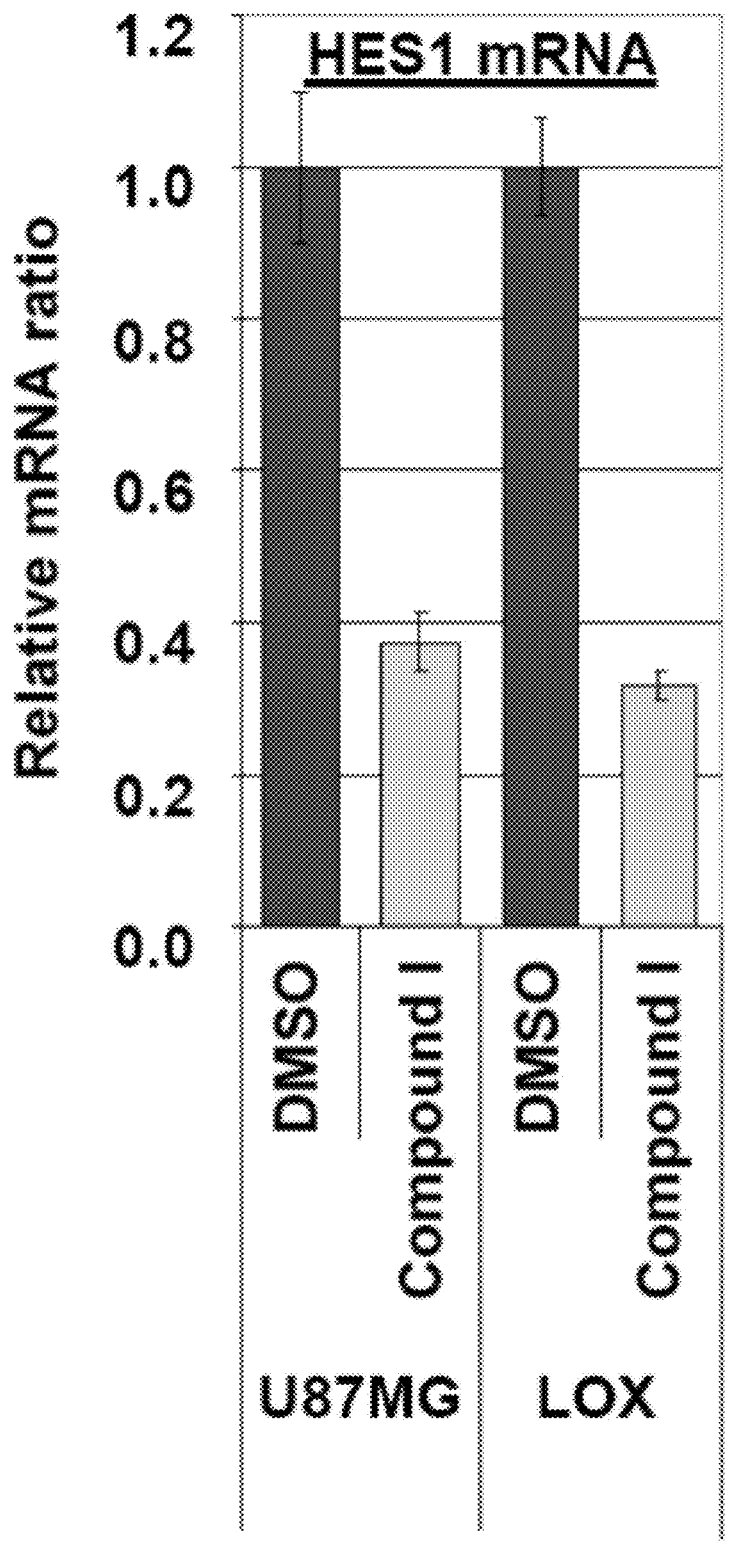
FIG. 13 depicts the effect of Compound I treatment on tumor growth in U87MG and LOX cells.

The resistance of the U87MG and LOX cells to Compound I was not caused by a loss of Notch inhibition since down-regulation of Hes1 mRNA following in vitro Compound I treatment, the hallmark of Notch signaling blockage, was properly maintained in these cells. See FIG. 13.

Example 10

Serum levels of IL6 and IL8 in xenograft models were measured to determine whether they reflect the expression differences observed in vitro from cell media. The resulting data suggest that serum collection could be a clinically viable approach to monitoring patient tumor levels of IL6 and IL8.

Mouse sera were collected from tumor bearing mice using the following xenograft models: A549, H460a, IL8-knockdown H460a, U87MG and LOX (models were produced using the methods described above). This was accomplished by retro-orbital bleeding or cardiac puncture in BD Microtainer serum separator tubes (Catalog #365956, Becton Dickinson, Franklin Lakes, N.J.). The blood was allowed to clot for a minimum of 10 minutes and spun down at 9000 rpm for 10 minutes in a microcentrifuge. The serum was collected and placed in 1.5 ml microcentrifuge tubes and stored at −80° C.

Figure 14:
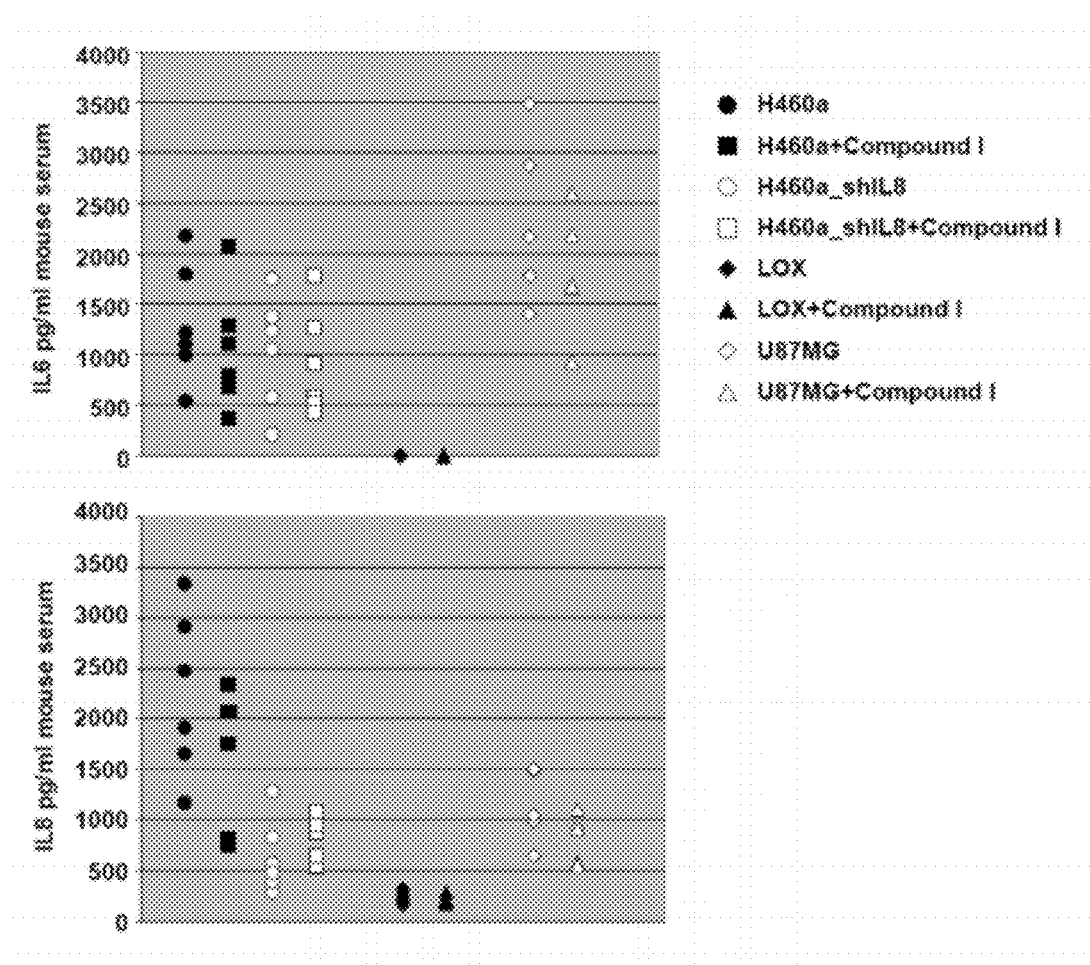
FIG. 14 depicts the amount of secreted IL6 and IL8 measured using ELISA in H460a cells, H460a cells treated with Compound I, IL8-knockdown H460a cells, IL8-knockdown H460a cells treated with Compound I, U87MG cells, and U87MG cells treated with Compound I.

Secreted human IL6 and IL8 in the mouse sera from A549 tumors were too low to be detected by ELISA. However, human IL6 and IL8 originating from H460a, LOX and U87MG xenograft models was readily detected in serum using ELISA (FIG. 14). In addition, expected changes in secreted IL8 serum levels were observed between the IL8-knockdown H460a model and the H460a model.

In general, levels of IL6 and IL8 observed in vivo in serum reflected the amounts observed in vitro from cell cultures. However, we did observe some discrepancy between IL6 and IL8 measured from mouse sera versus from cell media. For example, U87MG secreted 5-6 fold higher levels of IL6 and IL8 than H460a when seeded at the same numbers of cells on plastic; this was not reflected in mouse sera.

The invention claimed is:

1. A method for determining the resistance of a subject suffering from a non-small cell lung carcinoma to treatment with 2,2-Dimethyl-N-((S)-6-oxo-6,7-dihydro-5H-dibenzo[b,d]azepin-7-yl)-N'-(2,2,3,3,3-pentafluoro-propyl)-malonamide, comprising measuring the level of a biomarker present in a biological sample of serum obtained from said subject, said biomarker being IL6 or IL8.

2. A method according to claim 1, wherein said subject is a mammal.

3. A method according to claim 1, wherein said subject is a human.

4. A method according to claim 1, wherein said biomarker is IL6.

5. A method according to claim 1, wherein said biomarker is IL8.

6. A method according to claim 1, wherein the levels of both IL6 and IL8 are measured.

7. A method according to claim 1, wherein said biomarker is measured by measuring the amount of protein present in said sample.

8. A method according to claim 1, wherein said biomarker is measured by measuring the level of mRNA encoding said biomarker.

9. A method according to claim 1 wherein the level of biomarker present in said sample is compared with a threshold level for said biomarker and, if greater, said subject is considered to have in vivo resistance to treatment with 2,2-Dimethyl-N-((S)-6-oxo-6,7-dihydro-5H-dibenzo[b,d]azepin-7-yl)-N'-(2,2,3,3,3-pentafluoro-propyl)-malonamide.

10. A method according to claim 9 wherein said biomarker is IL6 and said threshold level for IL6 is about 500 pg/ml.

11. A method according to claim 9 wherein said biomarker is IL8 and said threshold level for IL8 is about 50 pg/ml.

* * * * *